(12) United States Patent
Raatschen et al.

(10) Patent No.: US 9,073,002 B2
(45) Date of Patent: Jul. 7, 2015

(54) METHOD FOR SEPARATING OFF CARBON DIOXIDE IN BIOGAS PLANTS

(75) Inventors: Willigert Raatschen, Immenstaad (DE); Carsten Matthias, Friedrichshafen (DE); Karlheinz Brodt, Immenstaad (DE); Manuela Brodt, legal representative, Immenstaad (DE); Joachim Lucas, Großschönach (DE)

(73) Assignee: Airbus DS GmbH, Taufkirchen (DE)

( * ) Notice: Subject to any disclaimer, the term of this patent is extended or adjusted under 35 U.S.C. 154(b) by 130 days.

(21) Appl. No.: 13/876,785

(22) PCT Filed: Oct. 5, 2011

(86) PCT No.: PCT/EP2011/004948
§ 371 (c)(1),
(2), (4) Date: Oct. 14, 2013

(87) PCT Pub. No.: WO2012/045442
PCT Pub. Date: Apr. 12, 2012

(65) Prior Publication Data
US 2014/0053724 A1  Feb. 27, 2014

(30) Foreign Application Priority Data
Oct. 8, 2010  (EP) .................................... 10013451

(51) Int. Cl.
*B01D 53/04* (2006.01)
*C12M 1/00* (2006.01)

(52) U.S. Cl.
CPC ............ *B01D 53/0454* (2013.01); *B01D 53/04* (2013.01); *B01D 53/0407* (2013.01);
(Continued)

(58) Field of Classification Search
CPC ........... B01D 2253/20; B01D 2256/24; B01D 2257/504; B01D 2258/05; B01D 2259/40009; B01D 53/04; B01D 53/0407; B01D 53/0454; C12M 47/18; Y02C 10/08
See application file for complete search history.

(56) References Cited

U.S. PATENT DOCUMENTS 4,425,143 A * 1/1984 Nishizawa et al. ............. 95/126
5,389,125 A   2/1995 Thayer et al.
(Continued)

FOREIGN PATENT DOCUMENTS

DE   19830470 C1   11/1999
GB   2020191 A    11/1979
(Continued)

OTHER PUBLICATIONS

International Search Report and Written Opinion of the International Searching Authority mailed Jan. 16, 2012 for the corresponding international application No. PCT/EP2011/004948 (with English translation).
(Continued)

*Primary Examiner* — Christopher P Jones
(74) *Attorney, Agent, or Firm* — Posz Law Group, PLC

(57) ABSTRACT

A method for separating off carbon dioxide in biogas plants includes an adsorption phase and a regeneration phase. Crude biogas that is treated in the adsorption phase is passed at ambient pressure through an adsorber suitable for adsorption of carbon dioxide, and in the regeneration phase the adsorber is regenerated with a purge gas at the temperature between 20 and 100° C., and also ambient pressure. The crude biogas is treated upstream of the carbon dioxide separation method, and is desulphurized and dried and minor components can be removed. For avoiding impurities in the biogas, at the start of the adsorption phase a purge process is carried out on the adsorber with treated crude biogas, wherein the purge process is controlled with respect to time via a number of valves and a sensor.

14 Claims, 2 Drawing Sheets

(52) U.S. Cl.
CPC ......... *B01D2253/20* (2013.01); *B01D 2256/24* (2013.01); *B01D 2257/504* (2013.01); *B01D 2258/05* (2013.01); *B01D 2259/40009* (2013.01); *Y02C 10/08* (2013.01); *C12M 47/18* (2013.01)

(56) References Cited

U.S. PATENT DOCUMENTS

| | | | |
|---|---|---|---|
| 5,797,979 A | | 8/1998 | Quinn |
| 2010/0024647 A1* | | 2/2010 | Gunther .......................... 95/183 |
| 2011/0072965 A1* | | 3/2011 | Lie et al. ............................ 95/47 |
| 2011/0174156 A1* | | 7/2011 | Saunders et al. .................. 95/46 |

FOREIGN PATENT DOCUMENTS

| | | |
|---|---|---|
| WO | 98/58726 A1 | 12/1998 |
| WO | 2008/072215 A2 | 6/2008 |

OTHER PUBLICATIONS

International Preliminary Report on Patentability issued from the International Searching Authority mailed Apr. 9, 2013 for the corresponding international application No. PCT/EP2011/004948 (with English translation).

European Search Report issued from the European Patent Office dated Mar. 10, 2011 for the corresponding European application No. 10013451.9 (with Partial English translation).

European office action issued from the European Patent Office dated Jan. 10, 2012 for the corresponding European patent application No. 10013451.9 (with Partial English translation).

European Summons to attend Oral Proceedings issued from the European Patent Office dated Mar. 18, 2013 for the corresponding European patent application No. 10013451.9 (with English translation).

Telephone Consultation mailed on Oct. 4, 2013 regarding corresponding EP application No. 10 013 451.9 (and English Translation).

Ruthven D M, "Adsorption Separation Processes", Principles of Adsorption and Adsorption Processes, 1984, pp. 336-343 (Cited in the PCT Search Report and European office action).

European Search Report issued from the European Patent Office dated Jan. 10, 2012 for the corresponding European application No. 10013451.9.

European office action issued from the European Patent Office dated Mar. 18, 2011 for the corresponding European patent application No. 10013451.9.

International Search Report of the International Searching Authority mailed Jan. 16, 2012 for the corresponding international application No. PCT/EP2011/004948 (with English translation).

\* cited by examiner

METHOD FOR SEPARATING OFF CARBON DIOXIDE IN BIOGAS PLANTS

CROSS REFERENCE TO RELATED APPLICATIONS

This application is a U.S. national stage application of PCT/EP2011/004948 filed on Oct. 5, 2011, and claims priority to, and incorporates by reference, European patent application No. 10013451.9 filed on Oct. 8, 2010.

TECHNICAL FIELD

The invention relates to a method for separating off carbon dioxide in biogas plants.

BACKGROUND

For the process gases in a biogas plant, first of all, the following are defined:
Crude biogas: process gas which is withdrawn from the fermenter.
Processed crude biogas: crude biogas which has already passed through a biogas desulfurization and gas drying, but not a $CO_2$-separation stage.
Biogas: process gas which, after the $CO_2$-separation, predominantly comprises biomethane. The biogas can be fed into the natural gas grid after corresponding conditioning and compression.

It is known to process crude biogas from fermentative production and obtain biomethane as biogas. The crude biogas, depending on the composition of the substrate of the biogas plant, contains methane concentrations of approximately 40-75% by volume and carbon dioxide in a concentration range from approximately 25 to 55% by volume. The crude biogas is saturated with water vapor at the fermentation temperature and can have additional minor components. The processing of the crude biogas therefore comprises for the most part the following three method steps, biogas desulfurization, gas drying and $CO_2$-separation. The biogas can, after corresponding conditioning and compression, subsequently be fed into the natural gas grid.

For $CO_2$-separation, adsorptive separation methods are known, using zeolites (WO09/58726 or WO2008/072215) or carbon molecular sieves, and also absorptive separation methods such as physical scrubbing by means of water or Genosorb® or chemical scrubbing using MEA, DEA or MDEA. For said methods, depending on usage of the adsorber or absorber, either the $CO_2$ is separated off from the methane at high pressure of 4-7 bar, and regeneration of the adsorber or absorber is connected downstream at a low pressure (pressure-swing method), or the $CO_2$ is bound at low temperature and the adsorber or absorber is regenerated at high temperature (temperature-swing method). Regeneration of adsorbed $CO_2$ by way of moderate temperatures or application of a vacuum is disclosed by U.S. Pat. No. 5,797,979. Said pressure- and temperature-swing methods are energy-intensive.

SUMMARY

It is an object of the invention to specify an improved method for separating off carbon dioxide in biogas plants. Advantageous embodiments of the invention are the subject matter of subclaims.

This object is achieved by a method which comprises an adsorption phase for separating off carbon dioxide from processed crude biogas and also a regeneration phase. In the adsorption phase, processed crude biogas is passed at ambient pressure through an adsorber made of adsorber resin suitable for the adsorption of carbon dioxide, and in the regeneration phase the adsorber is regenerated with a purge gas at temperatures between 20 and 100° C. and also ambient pressure. The crude biogas is processed before the carbon dioxide is separated off, wherein the crude biogas is desulfurized and dried and minor components are removed. To avoid impurities in the biogas at the start of the adsorption phase, a purge process is carried out on the adsorber using processed crude biogas, wherein the purge process is controlled with respect to time via a number of valves and a sensor.

The regeneration time of the regeneration phase can be affected by the process parameters temperature and volumetric flowrate of the purge gas used during the regeneration, e.g. air or inert gas. The process parameters in this case are expediently selected in such a manner that a regeneration as complete as possible of the adsorber material is achieved and at the same time the energy expended for the regeneration is moderate.

BRIEF DESCRIPTION OF THE DRAWINGS

The invention and advantageous embodiments of the invention are described in more detail in drawings.

DETAILED DESCRIPTION

Figure 1:
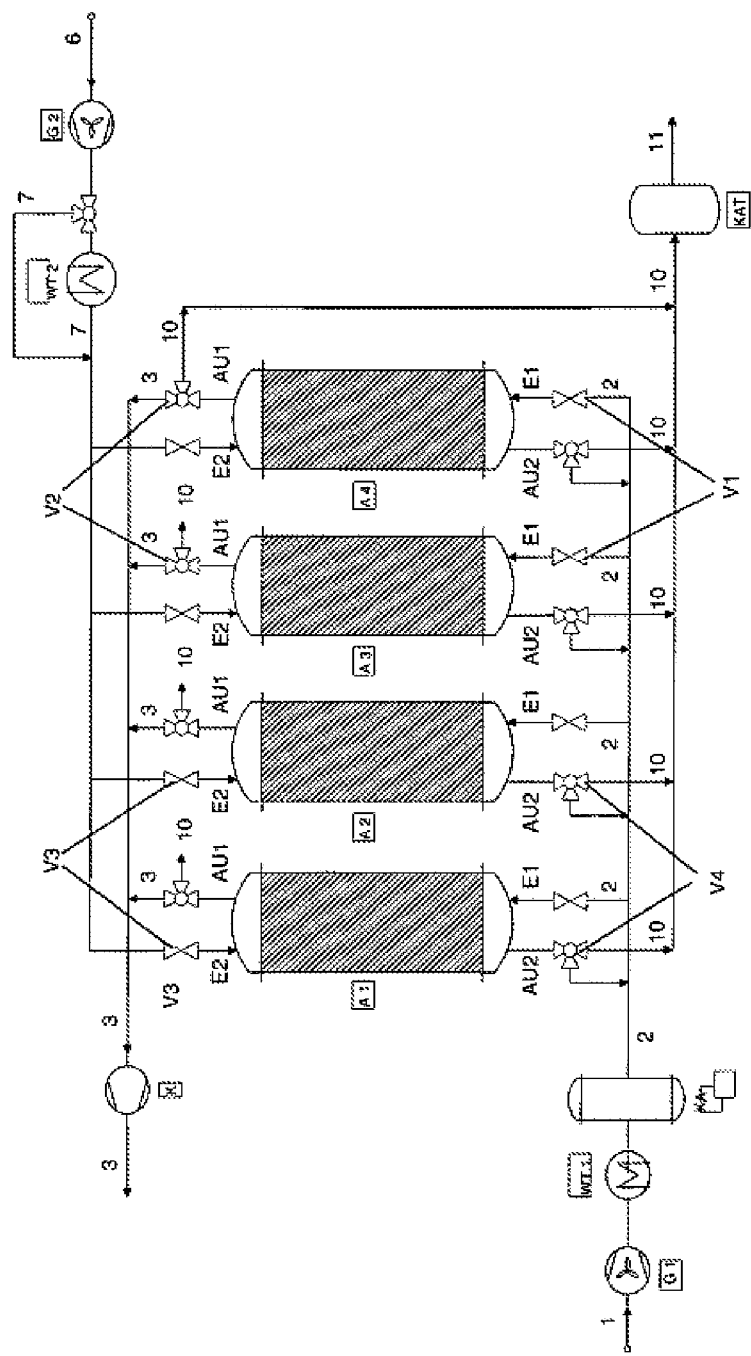
FIG. 1 is a schematic view of a device for carrying out the method according to the invention.

FIG. 1 shows a device for carrying out the method according to the invention, having four adsorbers A1 to A4. The number of the adsorbers can be varied according to the plant size.

Expediently, at the same time in the process, on the one hand, at least one or several adsorbers are in the adsorption phase and processed crude biogas 2 flows through them, and on the other hand, at least one or several adsorbers are in the regeneration phase and are loaded with a purge gas 7. The purge gas 7 can be fed for this purpose to the process plant by a blower G2 and be moderately preheated with an additional heat exchanger WT2.

The adsorption phase will be illustrated hereinafter with reference to FIGS. 1 and 2.

In the adsorption phase, desulfurized crude biogas 1 is fed by a blower G1 to the adsorbers A1 to A4. In this case, the desulfurized crude biogas 1 first passes through a heat exchanger WT1 having condensate separator KA, for gas drying. Subsequently, the gas can be purified in an activated carbon unit (not shown in FIG. 1) by removing minor components, such as hydrocarbons.

Subsequently, the processed crude biogas 2 is fed to the adsorbers A1 to A4 via the intake E1.

During the adsorption phase, the processed crude biogas 2 passes though the adsorber bed AB (FIG. 2) and leaves the adsorber container B as biogas via the exit AU1. At the start of the adsorption phase, valve V1 is open. The position of the valve V2 is selected in such a manner that the biogas 3 which, after it has passed through the adsorber, has a high purity of biomethane, can be fed into a compressor K according to FIG. 1 and subsequently to the natural gas grid. The valves V3 and V4 are closed in the adsorption phase.

Figure 2:
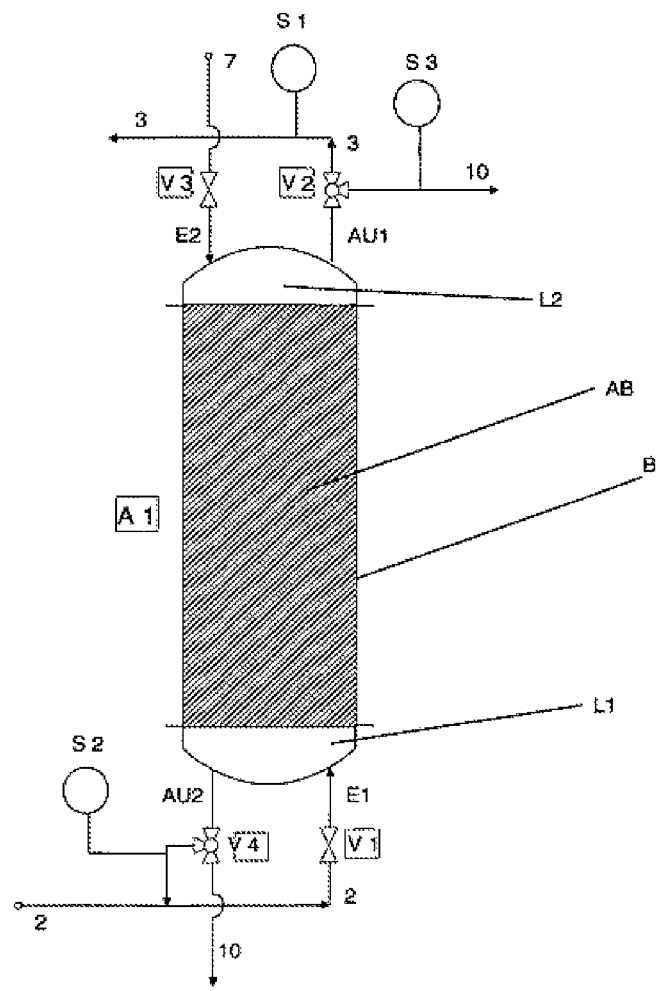
FIG. 2 is a view of a single adsorber of FIG. 1.

In the biogas 3 the $CO_2$ concentration is monitored during the adsorption according to FIG. 2 using the sensor S1 and the adsorption process is stopped when a predetermined $CO_2$ impurity is measured in the biogas 3 after it passes through the adsorber. At the end of the adsorption process, the valves V1 and V2 are closed.

Hereinafter, the regeneration phase is illustrated with reference to FIGS. 1 and 2.

After the adsorption phase, the $CO_2$-loaded adsorber bed AB is regenerated. For this purpose, first inert gas, and then air, can be passed as purge gas 7 into the adsorber bed AB via the intake E2 and through the open valve V3 (FIGS. 1 and 2). The air can be moderately preheated by means of the heat exchanger WT2.

In order to minimize methane losses during the regeneration phase, at the start of the regeneration the position of valve V4 is selected in such a manner that at the start of the regeneration phase, the gas leaving adsorbers A1 to A4 that still contains large fractions of methane at the start of the regeneration can be returned to the processed crude biogas 2. The methane can then be obtained as biogas 3 in another adsorber which is in the adsorption at the same time.

In the process gas at the exit AU2, after passage through the adsorber bed AB, the methane concentration is determined by the sensor S2. If the measured methane concentration falls below a preset value, the valve position V4 is selected in such a manner that subsequently air together with the desorbing $CO_2$ is discharged to the environment 11 as off-gas 10 during the regeneration phase. The off-gas 10 which still contains small amounts of methane can additionally be fed to a catalytic burner KAT. The waste heat of the catalytic burner KAT can be utilized for increasing the efficiency in a biogas plant.

After a preset time, the regeneration phase with preheated air 7 is ended and ambient air can be conducted past heat exchanger WT2 as purge gas 7 (FIG. 1) and the adsorber bed AB cooled before the start of the next adsorption phase. The adsorber bed AB can additionally be flooded with an inert gas as purge gas 7. The valves V3 and V4 are closed at the end of the regeneration phase.

Following the regeneration, the next adsorption phase is started. For this purpose, the valve V1 is then again opened and the processed crude biogas 2 is fed to the regenerated adsorber bed AB. At the start of the adsorption phase, the valve V2 is switched in such a manner that the air initially still situated in the adsorber container B or inert gas of the preceding regeneration phase can be discharged as off-gas 10 and thus gas impurities in the biogas 3 are minimized. In this case the methane concentration in the off-gas 10 is monitored at the exit AU1 of the adsorber by the sensor S3 (FIG. 2). When the measured methane concentration at the sensor S3 reaches a preset value, the valve V2 is switched over in such a manner that subsequently the gas flowing out of the exit AU1 of the adsorber can be reused as biogas 3 having high methane purities.

The unpressurized method according to the invention promises, using a $CO_2$-adsorber resin, the advantages of a high product purity and biogas yield similar to the known chemical scrubbing methods. By means of the regeneration with air at moderate temperatures, in addition, the energy expenditure of the method can be markedly lower than in previously known $CO_2$-separation methods.

The geometry of the adsorber container B can be freely selected and is not subject to the restrictions which result from a pressure- or temperature-swing load. The adsorber container B is expediently constructed so as to be cylindrical with as large a bed diameter as possible in order to achieve low flow velocities in the adsorber bed AB and to minimize the pressure drops of the plant. The height of the adsorber bed AB can be dimensioned in such a manner that a sharp separation of $CO_2$ and methane is achieved at the exit AU1 of the adsorber A1 to A4.

The wall material of the container B for the adsorber resin is freely selectable (e.g. metal, plastic) and is selected according to economic and processing aspects. Above and below the adsorber bed AB there is situated an empty space L1, L2 in the adsorber container B in order to tolerate a slight swelling of the adsorber resin and to ensure uniform flow distribution in the container B and in the adsorber bed AB. Likewise, a device for flow distribution is possible at the container intake and exit (which is not shown).

In addition, the adsorber can be provided with a device (which is not shown) by which the heat of adsorption released during the adsorption is recovered and returned to the biogas process.

The invention claimed is:

1. A method for separating off carbon dioxide in biogas plants comprising:
    preparing crude biogas for processing by drying and desulfurizing the crude biogas and removing minor components to obtain a processed crude biogas,
    an adsorption phase in which the carbon dioxide is separated off from the processed crude biogas in an adsorber and a biomethane obtained is fed into a natural gas grid as biogas, and
    a regeneration phase in which the adsorber is regenerated and the carbon dioxide that has been separated from the processed crude biogas is fed to ambient air or into a $CO_2$ storage,
    wherein,
    at the start of the adsorption phase, a purging process is carried out on the adsorber to avoid introducing impurities into the processed crude biogas, the purging process includes feeding into the adsorber an off gas discharged during a previous regeneration phase treatment of the adsorber, and the purging process is controlled at least with respect to time by using a plurality of valves and at least one sensor,
    in the adsorption phase, the processed crude biogas is passed at ambient pressure through the adsorber which contains an adsorber resin suitable for the adsorption of carbon dioxide,
    in the regeneration phase the adsorber is regenerated at temperatures between 20 and 100° C. and at ambient pressure using a preheated purge gas selected from the group consisting of air, an inert gas and a mixture thereof,
    at an end of the regeneration phase, the adsorber is cooled by purging with ambient air, and
    during the regeneration phase, an off gas exiting the absorber and containing air, desorbed carbon dioxide and small amounts of methane is fed into a catalytic burner and heat generated within the catalytic burner by the off gas is used for increasing efficiency in the biogas plant.

2. The method as claimed in claim 1, wherein heat of adsorption released during the adsorption phase is fed to a heat storage or heat exchanger.

3. The method as claimed in claim 1,
    wherein during the adsorption phase, to avoid $CO_2$ impurities in biogas exiting the adsorber, the $CO_2$ concentration at an exit of the adsorber is measured by a sensor and adsorption time is controlled via the measured $CO_2$ concentration in the adsorber-exiting biogas by a number of valves at an intake and the exit of the adsorber.

4. The method as claimed in claim 1,
wherein in the regeneration phase, a purge medium is passed through the adsorber and released into ambient air, and
wherein at the start of the regeneration phase, gas situated in the adsorber is added to the processed crude biogas.

5. The method as claimed in claim 2,
wherein during the adsorption phase, to avoid $CO_2$ impurities in biogas exiting the adsorber, the $CO_2$ concentration at an exit of the adsorber is measured by a sensor and adsorption time is controlled via the measured $CO_2$ concentration in the adsorber-exiting biogas by a number of valves at an intake and the exit of the adsorber.

6. The method as claimed in claim 2,
wherein in the regeneration phase, a purge medium is passed through the adsorber and released into ambient air, and
wherein at the start of the regeneration phase, gas situated in the adsorber is added to the processed crude biogas.

7. The method as claimed in claim 3,
wherein in the regeneration phase, a purge medium is passed through the adsorber and released into ambient air, and
wherein at the start of the regeneration phase, gas situated in the adsorber is added to the processed crude biogas.

8. A method for separating off carbon dioxide in biogas plants, comprising:
preparing a crude biogas for processing by drying and desulfurizing the crude biogas and removing minor components from the dried and desulfurized biogas;
adsorption phase processing that includes:
purging an adsorber to avoid, introducing impurities into the processed crude biogas, the purging includes feeding into the adsorber an off gas discharged during a previous regeneration phase treatment of the adsorber, and the purging being controlled at least with respect to time by using a plurality of valves and at least one sensor,
passing the processed crude biogas through the adsorber at ambient temperature and removing carbon dioxide from the crude biogas by adsorbing the carbon dioxide onto the adsorber, the adsorber comprising an adsorber resin suitable for the adsorption of carbon dioxide, and
feeding treated biogas exiting the adsorber having a decreased concentration of the carbon dioxide and an increased concentration of biomethane into a natural gas grid as a fuel; and
regeneration phase processing that includes:
preheating a purge gas selected from the group consisting of air, inert gas and mixtures thereof,
regenerating the adsorber having the carbon dioxide absorbed therein by desorbing the carbon dioxide from the adsorber at an ambient temperature and at a temperature between 20° C. and 100° C. using the preheated purge gas,
feeding an off gas exiting the absorber which contains air, desorbed carbon dioxide and small amounts of methane into a catalytic burner and using heat generated within the catalytic burner by the of gas for increasing efficiency in the biogas plant,
cooling the adsorber at the end of the regeneration phase processing using a purge gas including ambient air, and
feeding the removed carbon dioxide into ambient air or into a carbon dioxide storage.

9. The method as claimed in claim 8, wherein heat of adsorption released during the adsorption phase processing is fed to a heat storage or heat exchanger.

10. The method as claimed in claim 8,
wherein during the adsorption phase, to avoid carbon dioxide impurities in biogas exiting the adsorber, the carbon dioxide concentration at an exit of the adsorber is measured by a sensor and the adsorption time is controlled via the measured carbon dioxide concentration in the adsorber-exiting biogas by a number of valves at an intake and the exit of the adsorber.

11. The method as claimed in claim 8,
wherein in the regeneration phase, a purge medium is passed through the adsorber and released into ambient air, and
wherein at the start of the regeneration phase, methane retained in the adsorber is added to the processed crude biogas.

12. The method as claimed in claim 9,
wherein during the adsorption phase, to avoid carbon dioxide impurities in biogas exiting the adsorber, the carbon dioxide concentration at an exit of the adsorber is measured by a sensor and the adsorption time is controlled via the measured carbon dioxide concentration in the adsorber-exiting biogas by a number of valves at an intake and the exit of the adsorber.

13. The method as claimed in claim 9,
wherein in the regeneration phase, a purge medium is passed through the adsorber and released into ambient air, and
wherein at the start of the regeneration phase, methane retained in the adsorber is added to the processed crude biogas.

14. The method as claimed in claim 10,
wherein in the regeneration phase, a purge medium is passed through the adsorber and released into ambient air, and
wherein at the start of the regeneration phase, methane retained in the adsorber is added to the processed crude biogas.

* * * * *